US007220754B2

(12) United States Patent
Dijkstra et al.

(10) Patent No.: US 7,220,754 B2
(45) Date of Patent: May 22, 2007

(54) MONO-ESTER AND ASYMMETRICALLY SUBSTATUTED DI-ESTER PRO-DRUGS OF DOPAMIDE D1 RECEPTOR AGONISTS

(75) Inventors: Durk Dijkstra, VP Bedum (NL); Hakan Wikstrom, WN Groningen (NL)

(73) Assignee: DarPharma, Inc., Chapel Hill, NC (US)

( * ) Notice: Subject to any disclaimer, the term of this patent is extended or adjusted under 35 U.S.C. 154(b) by 38 days.

(21) Appl. No.: 10/503,796

(22) PCT Filed: Feb. 14, 2003

(86) PCT No.: PCT/US03/04592

§ 371 (c)(1),
(2), (4) Date: Aug. 6, 2004

(87) PCT Pub. No.: WO03/070245

PCT Pub. Date: Aug. 28, 2003

(65) Prior Publication Data

US 2005/0096469 A1 May 5, 2005

(30) Foreign Application Priority Data

Feb. 15, 2002 (SE) .................................. 0200478
Feb. 17, 2002 (SE) .................................. 0200474

(51) Int. Cl.
*A61K 31/473* (2006.01)
*A61K 31/4743* (2006.01)
*C07D 221/18* (2006.01)
*C07D 495/02* (2006.01)

(52) U.S. Cl. .......................... 514/284; 546/61; 546/62; 546/75; 514/285

(58) Field of Classification Search ................ 514/284, 514/285; 546/61, 62, 75
See application file for complete search history.

(56) References Cited

U.S. PATENT DOCUMENTS

| 4,282,227 | A | | 8/1981 | Brenner |
| 4,340,600 | A | | 7/1982 | Brenner et al. |
| 5,047,536 | A | * | 9/1991 | Nichols ....................... 546/61 |
| 5,420,134 | A | * | 5/1995 | Nichols et al. ............. 514/280 |
| 5,597,832 | A | * | 1/1997 | Michaelides et al. ....... 514/285 |
| 6,194,423 | B1 | | 2/2001 | Nichols et al. |

FOREIGN PATENT DOCUMENTS

| WO | WO 92/04356 | 3/1992 |
| WO | WO 94/22858 | 10/1994 |
| WO | WO 96/02513 | 2/1996 |

OTHER PUBLICATIONS

PCT International Search Report for PCT/US03/04592 completed by the U.S. Searching Authority on May 5, 2003.

C. Kaiser and T. Jain, "Dopamine Receptors: Functions, Subtypes and Emerging Concepts", Medicinal Research Reviews, 5:145-229, 1985.
D. Sibley and F. Monsma, "Molecular Biology of Dopamine receptors", in TIPS, vol. 13, pp. 61-69, 1992.
G.P. Reynolds, "Developments in the drug treatment of schizophrenia", in TIPS, :116-121, 1992.
M. Del Zompo et al, "Dopamine agonists in the treatment of schizophrenia", Progress in Brain Research, E:41-48, 1986 end.
M. Davidson, "Effects of the D-1 Agonist SKF-38393 Combined With Haloperidol in Schizophrenic Patients", Arch Gen. Psychiatry, 42:190-191, 1990.
R.A. Wise and P.P. Rompre in "Brain Dopamine and Reward", Annual Review of Psychology, 40:191-225, 1989.
D.R. Britton et al, "Evidence for Involvement of Both D1 and D2 Receptors in Maintaining Cocaine Self-Administration", Pharmacology Biochemistry & Behavior, 89:911-915, 1991.
R. Muscat et al., "Antidepressant-like effects of dopamine agonists in an animal model of depression", Biological Psychiatry, 31:937-946, 1992.
F. Levy, "The Dopamine Theory of Attention Deficit Hyperactivity Disorder (ADHD)", in Australian and New Zealand Journal of Psychiatry, 2:277-283, 1991.
Talley at al., Clin. Res., 18:518, 1970.
H.E. Katerinopoulos and D.I. Schuster, "Structure-Activity Relationships for Dopamine Analogs A Review", in Drugs Of The Future, vol. 12, pp. 223-253, 1987.
P.H. Anderson et al, European Journal of Pharmacology, 137:291-292, 1987.
W.K. Brewster al., "trans-1 0,11-dihydroxy-5,6,6a,7,8,1 2b-hexahydrobenzo[a]phenanthridine: A Highly Potent Selective Dopamine D1 Full Agonist", in Journal of Medicinal Chemistry, D:1756-1784, 1990.
H. Y. Meltzer, "Novel Approaches to the Pharmacology of Schizophrenia", Drug Development Research, 9:23-40, 1986.
Jenner, P., "The rationale for the use of dopamine agonists in Parkinson's disease" Neurology 45(3): S6-12 (1995).
Wolters, EC, et al., "Dopamine agonists in Parkinson's disease" Neurology 45(3): S28-S34 (1995).
Aldrich, MS, et al., "Dopamine-receptor autoradiography of human narcoleptic brain" Neurology 42(2):410-415 (1992).
Tintner R., and Jankovic J., "Assessment and Treatment of Parkinson's Disease" Clinical Geriatrics 09(01): 1070-1389 (2001).
Davis KL, et al., "Dopamine in schizophrenia: a review and reconceptualization" Am. J. Psychiatry 148:1474-1486 (1991).
Lynch, MR, "Schizophrenia and the $D_1$ receptor: focus on negative symptoms" Prog Neuro-psychopharmacol. Biol. Psychiatry 16(6):797-832 (1992).

(Continued)

*Primary Examiner*—Charanjit S. Aulakh
(74) *Attorney, Agent, or Firm*—Barnes & Thornburg LLP

(57) ABSTRACT

Mono-ester and asymmetrically substituted diesters of dihydrexidine, dinapsoline and A-86929 and substituted derivatives thereof are described. The novel ester/diester derivatives exhibit improved pharmacokinetic characteristics relative to their unesterified parent compounds and can be formulated into pharmaceutical compositions useful for the treatment of a wide variety of dopamine related disorders.

10 Claims, No Drawings

OTHER PUBLICATIONS

Castner, SA, et al., "Reversal of Antipsychotic Induced Working Memory Deficits by Short-Term Dopamine $D_1$ Receptor Stimulation" Science 287(5460):2020-2022 (2000).

Floresco SB, and Phillips, AG, "Delay-dependent modulation of memory retrieval by infusion of a dopamine $D_1$ agonist into the rat medial prefrontal cortex" Behav. Neurosci. 115(4):934-939 (2001).

Hersi, Al, et al., "Dopamine $D_1$ receptor ligands modulate cognitive performance and hippocampal acetylcholine release in memory-impaired aged rats" Neuroscience 69(4):1067-1074 (1995).

George TP, et al. "The potential of dopamine agonists in drug addiction" Expert Opinion on Investigational Drugs 11(4):491-499 (2002).

Britton DR, et al., "Evidence for involvement of both D1 and D2 receptors in maintaining cocaine self-administration" Pharmacol. Biochem. Behav. 39(4):911-5 (1991).

Jackson DM, et al., "Dopamine $D_2$ agonist-induced behavioural depression is reversed by dopamine $D_1$ agonists" Journal of Neural Transmission 75(3):213-220 (1989).

Cook, EH Jr., et al., "Association of attention-deficit disorder and the dopamine transporter gene" Am. J. Hum. Genet. 56(4):993-8 (1995).

Pliszka, Steven R. et al., "Catecholamines in Attention-Deficit Hyperactivity Disorder: Current Perspectives" J. Am. Acad. Child Adolesc. Psychiatry 35(3):264-272 (1996).

* cited by examiner

MONO-ESTER AND ASYMMETRICALLY SUBSTATUTED DI-ESTER PRO-DRUGS OF DOPAMIDE D1 RECEPTOR AGONISTS

CROSS REFERENCE TO RELATED APPLICATIONS

This application is a U.S. national counterpart application of international application serial No. PCT/US03/04592 filed Feb. 14, 2003, which claims priority to Swedish Patent Application No. 0200478-6 filed Feb. 15, 2002 and Swedish Patent Application No. 0200474-5 filed Feb. 17, 2002. The entireties of each of these applications are hereby incorporated by reference.

FIELD OF THE INVENTION

This invention relates to novel mono-ester and asymmetrically substituted di-ester pro-drugs of dopamine D1 receptor agonists, useful for treating dopamine-related neurological, psychological, cardiovascular, cognitive and behavioral disorders.

BACKGROUND OF THE INVENTION

Dopamine is an important neurotransmitter in the central nervous system (CNS), as where it is involved with motor function, perception, arousal, motivation and emotion. Dopamine imbalance is believed to play a key role in a number of CNS-related disorders such as schizophrenia, Parkinson's disease, drug abuse, eating disorders and depression. Dopamine also has several important roles in the peripheral nervous system, such as in the control of blood to the kidneys and in autotonomic ganglion transmission.

Dopamine receptors in the CNS have traditionally been divided into two general categories, designated D-1 and D-2 receptors, based on biochemical and pharmacological differences between the two receptor types, and more recently from the study of the molecular biology of dopamine receptors in the CNS. (For a review of the classification and function of dopamine receptor subtypes, see C. Kaiser and T. Jain, "Dopamine Receptors: Functions, Subtypes and Emerging Concepts", Medicinal Research Reviews, 5:145–229, 1985.) Recent additional evidence has suggested an even greater heterogeneity of the dopamine receptors with three additional dopamine receptors being defined through molecular cloning techniques: the D3 and D4, which are classified as D2-like, and the D5, which exhibits D1 receptor-like pharmacology (D. Sibley and F. Monsma, "Molecular Biology of Dopamine receptors", in TIPS, Vol. 13, pp. 61–69, 1992). Attempts to understand the physiological and pathophysiological roles of the various dopamine receptors are continuing to unveil new avenues for novel therapeutic approaches for the treatment of dopamine-related disorders.

A particular dopamine-related problem involves the loss of striatal dopamine within the basal ganglia, the region of the mammalian brain that is involved with motor control, which has been established as the fundamental deficit in Parkinson's Disease and primary to the etiology of that disease state.

This deficiency is addressed via dopamine replacement therapy, primarily with L DOPA (3,4-dihydroxyphenylalanine), which is converted to dopamine within the brain. L-DOPA has been the cornerstone of Parkinson's Disease therapy, and the successes achieved with its therapy have led to the testing of other compounds capable of eliciting the post-synaptic receptor actions of dopamine.

Bromocriptine, the most widely used direct-acting dopamine agonist for the treatment of Parkinson's Disease, is administered adjunctively with L-DOPA in order to lower dosage of L-DOPA required to achieve the desired therapeutic response. Bromocriptine alone has been shown to relieve Parkinson's Disease symptoms in some patients, allowing for a delay in the onset of L-DOPA therapy, but the response to bromocriptine alone is not as great as that observed with L DOPA. The current therapies for Parkinson's Disease, including L-DOPA and bromocriptine, are, however, unfortunately associated with a number of serious side-effects and limitations, such as the development of dyskinesias, severe response fluctuations (on-off phenomenon) and diminishing efficacy during treatment.

An excess of dopamine in the brain, on the other hand, has bean identified, as a result of the pioneering work of Carlsson and others in the 1960's, as the cause of schizophrenia, a psychiatric illness involving disturbance of thought processes, hallucinations and loss of touch with reality. Chronic abuse of stimulants, such as amphetamines, known to enhance dopaminergic activity in the brain, can lead to a paranoid psychosis that is clinically indistinguishable from classic paranoid schizophrenia, further supporting this dopamine theory of schizophrenia.

Anti-schizophrenic drugs are postulated to exert their effects by blocking the dopamine receptors (i.e., acting as receptor antagonists), and consequently preventing excess receptor stimulation (G. P. Reynolds, "Developments in the drug treatment of schizophrenia", in TIPS, :116–121, 1992). These antipsychotic agents frequently produce undesirable side-effects, however, the most common of which are the extrapyramidal effects that include bizarre involuntary movements and Parkinson-like states, as well as sedation and hypotension. Because of these often severe side-effects and the high incidence of patients unresponsive to dopamine blocking drugs, novel and improved therapies continue to be sought.

One such complement to dopamine receptor antagonists has included the use of low doses of dopamine agonists, such as apomorphine and bromocriptine. which have been reported to produce anti psychotic effects, possibly due to preferential activation of dopamine presynaptic receptors resulting in decreased dopaminergic activity (M. Del Zompo et al, "Dopamine agonists in the treatment of schizophrenia", Progress in Brain Research, E:41–48, 1986 end H. Y. Meltzer, "Novel Approaches to the Pharmacology of Schizophrenia", Drug Development Research, 9:23–40, 1986). In addition, the dopamine D1-selective agonist, SKF 38393, when used in conjunction with the antipsychotic drug, haloperidol, a D2 antagonist, has been shown to ameliorate the undesired side-effects of the haloperidol (M. Davidson, "Effects of the D-1 Agonist SKF-38393 Combined With Haloperidol in Schizophrenic Patients", Arch Gen. Psychiatry, 42:190–191, 1990).

Growing evidence (reviewed by R. A. Wise and P. P. Rompre in "Brain Dopamine and Reward", Annual Review of Psychology, 40:191–225, 1989) suggests that dopamine also has a central role in the brain's reward system. For example, animals trained to self-administer cocaine will increase their consumption of this drug after treatment with either a D-1 or a D-2 receptor antagonist, presumably in order to maintain the elevated dopamine levels responsible for the drug's euphorigenic and reinforcing properties (D. R. Britten et al, "Evidence for Involvement of Both D1 and D2 Receptors in Maintaining Cocaine Self-Administration", Pharmacology Biochemistry & Behavior, 89:911–915, 1991). The D-1 agonist, SKE 38393, has also been reported to decrease food intake by rats, presumably by direct action of the drug on neural feeding mechanisms. Because of this interrelationship between dopamine and reward, dopaminergic agents would be useful for the treatment of substance abuse and other addictive behavior disorders, including cocaine addiction, nicotine addiction and eating disorders.

Affective disorders, the most common psychiatric disorders in adults, which are characterized by changes in mood as the primary clinical manifestation, result from a reduction in the central nervous system of certain biogenic amine neurotransmitters, such as dopamine, noradrenaline and serotonin. Currently available antidepressants work primarily by raising biogenic amine neurotransmitter levels, by either inhibiting their uptake or preventing their metabolism. No antidepressant drug to date, however, can substitute for electroconvulsive shack therapy for the treatment of severe, suicidal depression.

Currently-available drugs for treating affective disorders, unfortunately, suffer from delayed onset of action, poor efficacy, anticholinergic effects at therapeutic doses, cardiotoxicity, convulsions and the possibility of overdosing. A large number of clinically depressed individuals remain refractory to currently-available therapies.

A role for direct-acting dopamine agonists in antidepressant therapy has been suggested based on the effects observed for several dopamine agonists In various animal models (R. Muscat et al., "Antidepressant-like effects of dopamine agonists in an animal model of depression", Biological Psychiatry, 31:937–946, 1992).

A role for dopamine has also been established in cognition and attention mechanisms. Animal studies support the role of dopamine in attention-related behaviors involving search and exploratory activity, distractibility, response rate, discriminability and the switching of attention. Treatment of cognitive impairment and attention deficit disorders via dopamine-based therapy has been proposed and is under active investigation (F. Levy, "The Dopamine Theory of Attention Deficit Hyperactivity Disorder (ADHD)", in Australian and New Zealand Journal of Psychiatry, 2:277–283, 1991).

In addition, dopamine has been identified with a number of effects in the periphery, and has been used in the treatment of shock, congestive heart failure and acute renal failure. Stimulation of the peripheral D-1 receptors causes vasodilation, particularly in the renal arid mesenteric vascular beds where large numbers of these receptors are found. The utility of dopamine has been limited, however, by its ability to cause vasoconstriction at higher concentrations, presumably due to its secondary effects on adrenergic receptors, and by its emetic effects due to peripheral D-2 stimulation. Agents selective for the peripheral D-1 receptors appear to offer significant advantages over currently used treatments for these and other related disorders.

Also, dopamine in combination with diuretics has been reported to reverse radio-contrast media-induced acute renal failure in patients (Talley at al., Clin. Res., 18:518, 1970); thus suggesting that dopamine agonists may be similarly useful.

A wide variety of structures has been disclosed that are dopamine receptor ligands (H. E. Katerinopoulos and D. I. Schuster, "Structure-Activity Relationships for Dopamine Analogs A Review", in Drugs Of The Future, Vol. 12, pp. 223–253, 1987) and include the thienopyridines, SKF 86926 (4-(3',4'-dihydroxyphenyl) 4,5,6,7-tetrahydrotheno (2,3-c)-pyridine) and SKF 86915 (7-(3',4'dihydroxyphenyl)-4,5,6, 7-tetrahydrothlieno (3,2-c)-pyridine) (P. H. Andersen et al, European Journal of Pharmacology, 137:291–292, 1987, U.S. Pat. No. 4,340,600, to L. M. Brenner and J. R. Wardell, Jr., issued 1982, and U.S. Pat No. 4,282,227, to L. M. Brenner, issued 1981). Nichols at al. have disclosed certain substituted trans-hexahydrobenzo[a]-phenanthridine compounds as dopaminergic ligands (U.S. Pat. No. 5,047,536, to D. E. Nichols, issued 1991; W. K. Brewster al., "trans-10, 11-dihydroxy-5,6,6a,7,8,12b-hexahydrobenzo[a]phenanthridine: A Highly Potent Selective Dopamine D1 Full Agonist", in Journal of Medicinal Chemistry, D:1756-1784, 1990).

U.S. Pat. Nos. 5,047,536 and 6,194,423, incorporated herein, describe and claim the dopamine D1 agonists dihydrexidine (Formula I) and dinapsoline (Formula II) and their optionally substituted derivatives, respectively. PCT/US94/02894 describes the dopamine D-1 agonist A-86929 (Formula III), its diacylated derivated form (Formula IV) and other optionally substituted derivatives of A-86929. For the purpose of describing and specifying this invention, Formulas I–III shall be representative of dihydrexidine, dinapsoline, A-86929, respectively, and the various N- and C-substituted derivatives thereof described in the above-mentioned patent literature.

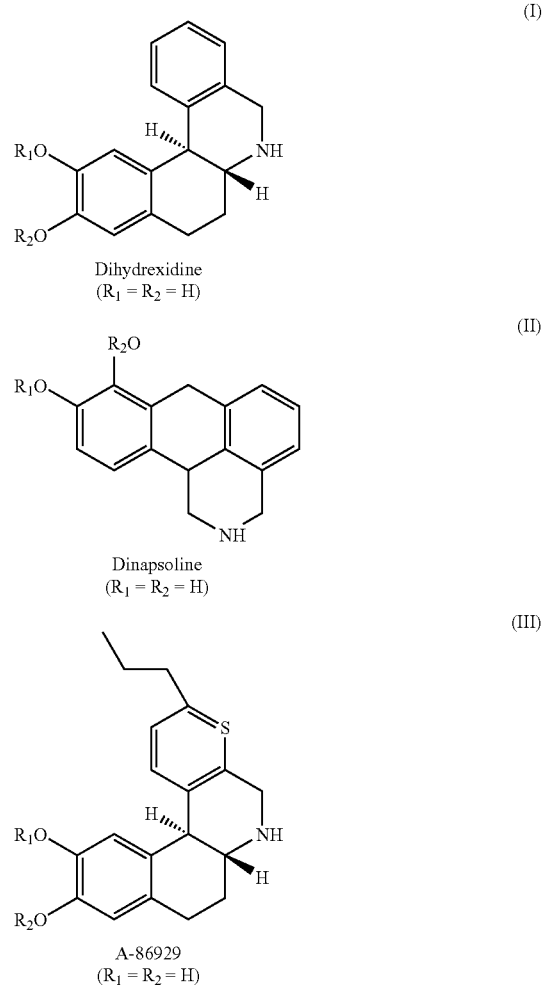

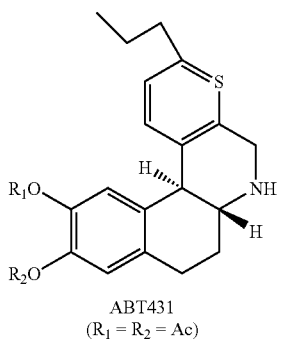

ABT431
(R₁ = R₂ = Ac)

Each of the "parent" compounds (R₁=R₂=H) of Formulas I–III and their D-1 receptor agonist substituted derivatives/analogs share a common structural feature: adjacent phenolic hydroxy groups. The present invention is directed to monoester and asymmetrically substituted diester derivatives of such compounds and their receptor agonist substituted derivatives and analogs, where either one of the hydroxy groups is acylated with an ester-forming group or each of the adjacent phenolic hydroxy groups is acylated with a different ester-forming group. The compounds of the present invention exhibit unexpectedly improved pharmacokinetic properties, as compared to the previous described unacylated "parent" compounds.

DETAILED DESCRIPTION OF THE INVENTION

The present invention is directed to mono-ester and asymmetrically substituted di-ester pro-drugs of the dopamine D1 agonists of Formulas I, II and III above and their optionally substituted derivatives wherein one of $R_1$ and $R_2$ is hydrogen or acetyl and the other one is selected from the group consisting of $(C_3-C_{20})$ alkanoyl; halo-$(C_3-C_{20})$alkanoyl; $(C_3-C_{20})$alkenoyl; $(C_4-C_7)$cycloalkanoyl; $(C_3-C_6)$ cycloalkyl$(C_2-C_{16})$alkanoyl; aroyl which is unsubstituted or substituted by 1 to 3 substituents selected from the group consisting of halogen, cyano, trifluoromethanesulphonyloxy, $(C_1-C_3)$alkyl and $(C_1-C_3)$alkoxy, which latter may in turn be substituted by 1 to 3 halogen atoms; aryl $(C_2-C_{16})$ alkanoyl which is unsubstituted or substituted in the aryl moiety by 1 to 3 substituents selected from the group consisting of halogen, $(C_1-C_3)$alkyl and $(C_1-C_3)$alkoxy, which latter may in turn be substituted by 1 to 3 halogen atoms; and hetero-arylalkanoyl having one to three heteroatoms selected from O, S and N in the heteroaryl moiety and 2 to 10 carbon atoms in the alkanoyl moiety and which is unsubstituted or substituted in the heteroaryl moiety by 1 to 3 substituents selected from the group consisting of halogen, cyano, trifluoromethanesulphonyloxy, $(C_1-C_3)$alkyl, and $(C_1-C_3)$alkoxy, which latter may in turn be substituted by 1 to 3 halogen atoms, and the physiologically acceptable salts thereof.

According to one embodiment of the present invention there is provided a compound for Formula I, II or III above or their optionally substituted derivatives, wherein one of $R_1$ and $R_2$ is hydrogen or acetyl and the other one is selected from the group consisting of $(C_3-C_{20})$alkanoyl, $(C_4-C_7)$ cycloalkanoyl, benzoyl which is unsubstituted or substituted by a chlorine atom or 1 to 3 methoxy groups, phenylacetyl which may be substituted with a chlorine atom, and heteroarylacetyl.

According to another embodiment of the present invention there is provided a compound of the general Formulas I, II or III above or their substituted derivatives, wherein one of $R_1$ and $R_2$ is hydrogen and the other is selected from the group consisting of propanoyl, propenoyl, butanoyl, isobutanoyl, pivaloyl, decanoyl, hexadecanoyl, cyclopropanoyl and benzoyl.

According to another embodiment of the present invention there is provided a compound of the Formulas I and II or III or their substituted derivatives, wherein one of $R_1$ and $R_2$ is acetyl and the other is selected from the group consisting of butanoyl, isobutanoyl, cyclopropanoyl, cyclohexanoyl, pivaloyl, decanoyl and hexadecanoyl.

With regard to the definition of $R_1$ and $R_2$ in Formulas I and II and III above, the following meanings generally apply:

The terms "halo" and "halogen" are used to designate fluorine, chlorine, bromine and iodine, preferably fluorine and chlorine.

The term "$(C_3-C_{20})$alkanoyl" is used to designate the residue of a saturated aliphatic carboxylic acid of 3 to 20 carbon atoms, the carbon chain of which may be straight or branched. Examples of such alkanoyl groups are e.g. propanoyl, isopropanoyl, butanoyl, 2-methylpropanoyl, pentanoyl, 3-methyl-butanoyl, pivaloyl, n-hexanoyl, n-heptanoyl, n-octanoyl, n-nonanoyl, n-decanoyl, palmitoyl, stearoyl and eicosanoyl.

The term "halo-$(C_3-C_{20})$alkanoyl" is used to designate a $(C_3-C_{20})$ alkanoyl group as defined above which is substituted by at least one halogen atom, preferably by 1 to 3 halogen atoms.

The term "$(C_3-C_{20})$alkenoyl" is used to designate the residue of an aliphatic carboxylic acid of 3 to 20 carbon atoms, the carbon chain of which may be straight or branched and which contains 1 to 3 conjugated or non-conjugated double-bonds. Examples of such alkenoyl groups are, e.g. acryloyl, methacryloyl, linoleoyl and linolenoyl.

The term "$(C_4-C_7)$cycloalkanoyl" is used to designate a group having the formula

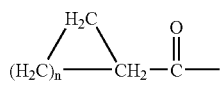

wherein n is an integer 1 to 4.

Such groups include cyclopropanoyl, cyclobutanoyl, cyclopentanoyl and cyclohexanoyl.

The term "$(C_3-C_6)$cycloalkyl–$(C_2-C_{16})$alkanoyl" is used to designate a group having the formula

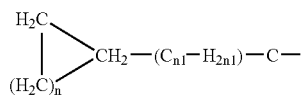

wherein n is defined as above, n1 is an integer 1 to 15, and the alkylene chain $(C_{n1}H_{2n1})$ may be straight or branched. Examples of such groups are, e.g. cyclopropyl acetyl, cyclohexyl acetyl, cyclopropyl hexanoyl and cyclopropyl palmitoyl.

The term "aroyl" is used to designate, for example, benzoyl, 1-naphthoyl and 2-naphthoyl. Said aroyl group is unsubstituted or substituted by 1 to 3 substituents selected from the group consisting of halogen, cyano, trifluoromethanesulphonyloxy, ($C_1$–$C_3$)-alkyl and ($C_1$–$C_3$)alkoxy, which alkyl and alkoxy groups in turn may be substituted by 1 to 3 halogen atoms. Examples of such substituted aroyl groups are m-methoxybenzoyl, p-trifluoromethoxybenzoyl. p-chlorobenzoyl, 3,4,5-trimethoxybenzoyl, p-cyanobenzoyl and 3-chloro-1-napthoyl.

The term "($C_1$–$C_3$)alkyl" is used to designate methyl, ethyl, propyl and isopropyl and the term "($C_1$–$C_3$)alkoxy" is used to designate methoxy, ethoxy, propoxy and isopropoxy.

The term "aryl-($C_2$–$C_{16}$)alkanoyl" is used to designate a group of the formula

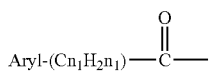

wherein Aryl and $n_1$ are as previously defined and the alkylene chain ($C_{n1}H_{2n1}$) may be straight or branched. The aryl moiety of said group may be substituted with substituents as indicated in connection with the aroyl groups above. Examples of aryl-($C_2$–$C_{16}$)alkanoyl groups are phenacetyl. p-chlorophenacetyl, p-trifluoromethoxyphenylacetyl and phenylhexanoyl.

Examples of hetero-arylalkanoyl groups having one to three heteroatoms selected from O, S and N in the heteroaryl moiety and 2 to 10 carbon atoms in the alkanoyl moiety and which are unsubstituted or substituted in the hetero-aryl moiety as indicated above are thiophen-2-yl-acetyl and pyrid-4-yl-hexanoyl.

The term "($C_1$–$C_4$)alkyl" is used to designate a straight or branched alkyl group of 1 to 4 carbon atoms including methyl, ethyl, propyl, isopropyl, butyl, 1-methyl propyl, 2-methyl propyl and t-butyl.

According to another aspect of the invention there are provided methods for the preparation of compounds of Formulas I, II and III above and their optionally substituted derivatives.

Accordingly, in one method embodiment, there is provided a process for the preparation of a mono-ester derivative of Formula I, II or III and derivatives thereof:

a) reacting a compound of Formula I, II or m (or a derivative thereof) with an acid chloride of the general formula:

$R_4$—Cl wherein $R_4$ is as defined for said other one of $R_1$ and $R_2$ above, in the molar ratio of the compound to acid chloride of from 1:1 to 1:5 and in trifluoracetic acid and methylene chloride ($CH_2Cl_2$);

b) after the reaction being completed, evaporating the solvents or lyophilizing the reaction mixture;

c) dissolving the residual crude product mixture in $CH_2Cl_2$ and purifying by chromatography on $Al_2O_3$ eluting with $CH_2Cl_2$ and then with t-BuOH:$CH_2Cl_2$ or EtOH:$CH_2Cl_2$ mixtures in a stepwise gradient of increasing concentration of t-BuOH and EtOH. respectively, of from 1 to 15% by volume, preferably from 2 to 10% by volume, of the mixture, and isolating fractions containing the isomeric mono-ester derivatives and d) optionally but preferably separating said isomeric mono-ester derivative products known techniques.

According to the present invention there is also provided a process for the preparation of di-ester derivatives of compounds of the general Formula I, II and III (or substituted derivatives thereof) wherein one of $R_1$ and $R_2$ is acetyl and the other one is selected from the group consisting of ($C_3$–$C_{20}$)alkanoyl; halo-($C_3$–$C_{20}$)alkanoyl; ($C_3$–$C_{20}$)alkenoyl: ($C_4$–$C_7$)cycloalkanoyl; ($C_3$–$C_6$)-cycloalkyl($C_2C_{16}$)alkanoyl; aroyl which is unsubstituted or substituted by 1 to 5 substituents selected from the group consisting of halogen, cyano, trifluoromethanesulphonyloxy, ($C_1$–$C_3$)alkyl and ($C_1$–$C_3$)alkoxy, which latter may in turn be substituted by 1 to 3 halogen atoms; aryl($C_2$–$C_{16}$)alkanoyl which is unsubstituted or substituted in the aryl moiety by 1 to 3 substituents selected from the group consisting of halogen, ($C_1$–$C_3$) alkyl and ($C_1$–$C_3$)alkoxy, which latter may in turn be substituted by 1 to 3 halogen atoms; and hetero-arylalkanoyl having one to three heteroatoms selected from O, S and N in the heteroaryl moiety and 2 to 10 carbon atoms in the alkanoyl moiety and which is unsubstituted or substituted in the heteroaryl moiety by 1 to 3 substituents selected from the group consisting of halogen, cyano, trifluoromethanesulphonyloxy, ($C_1$–$C_3$)alkyl, and ($C_1$–$C_3$)alkoxy, which latter may in turn be substituted by 1 to 3 halogen atoms; which process comprises a) reacting a mono-ester of one of the compounds of Formula I, II or III, wherein one of $R_1$ and $R_2$ is hydrogen and the other one is acetyl with an acid chloride of the general formula:

$R_5$—Cl wherein $R_5$ is as defined for said other one of $R_1$ and $R_2$ above, in the molar ratio of mono-ester to acid chloride of from 1:1 to 1:5 and trifluoroacetic acid and methylene chloride ($CH_2Cl_2$);

b) after the reaction being completed, evaporating the solvents or lyophilizing the reaction mixture;

c) dissolving the residual crude product mixture in $CH_2Cl_2$ and purifying by chromatography on $Al_2O_3$ eluting with $CH_2Cl_2$ and then with t-BuOH:$CH_2Cl_2$ or EtOH:$CH_2Cl_2$ mixtures in a stepwise gradient of increasing concentration of t-BuOH and EtOH, respectively, of from 1 to 16% by volume, preferably from 2 to 10% by volume, of the mixture, and isolating fractions containing the isomeric di-ester derivatives of the formula (1); and d) optionally, but preferably separating said isomeric di-ester derivatives by known techniques to isolate a single di-ester.

In a first modification of the method for the preparation of a di-ester derivative, a mono-ester of a compound of Formula I, II or m, wherein $R_1$ and $R_2$ are as defined above except that neither thereof is acetyl, is reacted with acetyl chloride in step a) in the molar ratio of mono-ester to acetyl chloride of from 1:1 to 1:6 and trifluoroacetic acid and methylene chloride ($CH_2Cl_2$), whereafter steps b) to d) as above follows.

In another modification of the method for the preparation of a di-ester derivative of Formula I, II or III or a substituted derivative thereof, a mono-ester wherein $R_1$ and $R_2$ are as defined above except that neither thereof is acetyl, is reacted in step a) with acetic acid anhydride in $CH_2Cl_2$ in the presence of a basic catalyst such as triethylamine or pyridine whereafter steps b) to d) as above follows.

Alternatively, a mono-acetyl ester is reacted with the anhydride of an acid of the formula $R_5$—OH wherein $R_5$ is as defined above, in a step a) in $CH_2Cl_2$ in the presence of a basic s catalyst such as triethylamine or pyridine whereafter steps b) to d) as above follows.

Catechols, are very sensitive to oxidation (e.g. in atmospheric air). This is especially true under basic conditions. It is thus virtually impossible to handle such catechols in the free base form, without the addition of antioxidants.

In addition, the pro-drugs of the present invention are designed to be easily hydrolyzed, making it difficult to use $SiO_2$ and nucleophilic alcohols for purification of the esters of the invention via column chromatography.

In step a) of the processes according to the present invention the esterification, for example of dihydrexidine or dinapsoline or its mono-acetyl ester, respectively, is performed under acidic conditions in trifluoroacetic acid ($CF_3COOH$) diluted with methylene chloride ($CH_2Cl_2$), a suitable dilution ratio being about 3–10 times. The acid chloride, possibly dissolved in $CH_2Cl_2$, is added to dihydrexidine or dinapsoline or its mono-acetyl ester, respectively, at a molar ratio between dihydrexidine or dinapsoline or its respective mono-ester to acid chloride of from 1:1 to 1:5. The optimal ratio will vary depending on the steric properties of the acid chloride but will generally be within the range of from 1:1 to 1:2.

The reaction can be monitored by means of thin layer chromatography ($Al_2O_3$ and eluting with $CH_2Cl_2$ or $CH_2Cl_2$:t-BuOH mixtures or $CH_2Cl_2$:EtOH mixtures).

After the reaction has become complete (generally within 1–24 h, depending on the acid chloride and molar ratio used) the solvents are evaporated from the reaction mixture or the reaction mixture is lyophilized in step b) of the processes of the invention. Evaporation of the solvents is generally carried out under reduced pressure.

For purification according to step c) of the processes of the present invention the residual crude product mixture from step b) is, in step c) dissolved in $CH_2Cl_2$ and purified, for example, by chromatography on $Al_2O_3$, elution being carried out by using first $CH_2Cl_2$ and then with mixtures of t-BuOH and $CH_2Cl_2$ in a stepwise gradient of increasing concentration of t-BuOH of from 1 to 15% by volume of t-BuOH calculated on the mixture, preferably from 2 to 10% by volume, for instance in steps of 1.0, 2.0, 5.0 and 10%. During the elution fractions containing the desired isomeric ester derivatives are collected.

The isomeric mono-esters may then be separated using known techniques such as flash chromatography, preparative HPLC (High Performance Liquid Chromatography), crystallization and other methods known per se. However, some of the isomeric mono-esters may prove difficult to separate and in such a case the mixture of the two isomers may be used as the starting material for the preparation of asymmetric di-esters or as the active principle in a pharmaceutical preparation.

In case of the preparation of the asymmetric di-esters, starting from an individual mono-ester isomer, the asymmetric di-esters will typically elute first and unreacted mono-esters thereafter.

Also in this case, when starting from a mixture of the two possible isomers of the mono-ester resulting from the esterification process of the present invention, the two di-ester isomers may prove difficult to separate and so it may appear advantageous to use the mixture of isomers as the active principle in a pharmaceutical preparation rather than taking the cost for the separation of the isomers.

According to a further aspect of the present invention there is provided a pharmaceutical composition comprising, as an active principle, at least one mono-ester or asymmetric di-ester of a compound of Formulas I, II and III as defined above (including optionally substituted derivatives) or a physiologically acceptable salt thereof together with a pharmaceutically acceptable carrier, diluent or excipient.

The term "at least one" as used in the paragraph next above is primarily meant to refer to the case when the mixture of two isomers resulting from the esterification process of the present invention is difficult to separate and hence it might appear advantageous to use said mixture rather than a single isomer. It might also appear advantageous to use the mixture of the two isomers or a combination of two compounds according to the invention having different combinations of the meanings of the symbols $R_1$ and $R_2$ in Formulas I, II and III between each other.

The ester pro-drugs of Formulas I, II and III and their optionally substituted derivatives, according to the invention may be incorporated in the pharmaceutical composition according to the invention as the base or as an acid addition salt, especially the hydrochloride salt. Other suitable salts are those formed by the acids HBr and sulphonic acids like methanesulphonic acid, octanesulphonic acid and hexadecansulphonic acid.

The term "administration" of the dopaminergic agent or composition, as used herein, refers to systemic use, as when taken orally, parenterally, by inhalation spray, by nasal, rectal or buccal routes, or topically in dosage form unit formulations containing conventional nontoxic pharmaceutically-acceptable carriers, adjuvants and vehicles, as desired.

The term "parenteral" as used herein includes intravenous, intramuscular, intraperitoneal, intrasternal, subcutaneous and intraarticular injection and infusion techniques.

By "pharmaceutically-acceptable" is meant those salts and esters, which are within the scope of sound medical judgment, suitable for use in contact with the tissues of humans and lower animals without undue toxicity, irritation, allergic response and the like, and are commensurate with a reasonable benefit/risk ratio, effective for their intended use in the treatment of psychological, neurological, cardiovascular and addictive behavior disorders.

As used herein, the term "pharmaceutically-acceptable carriers" means a nontoxic, inert solid, semi-solid or liquid filler, diluent, encapsulating material or formulation auxiliary of any type. Some examples of the materials that can serve as pharmaceutically-acceptable carriers are sugars, such as lactose, glucose and sucrose: starches, such as corn starch and potato starch; cellulose and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogenfree water; isotonic saline; Ringers solution; ethyl alcohol and phosphate buffer solutions, as well as other non-toxic compatible substances used in pharmaceutical formulations. Wetting agents, emulsifiers and lubricants, such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. Examples of pharmaceutically-acceptable antioxidants include water-soluble antioxidants, such as ascorbic acid, cysteine hydrochloride, sodium bisulfite, sodium metabisulfite, sodium sulfite, and the like; oil soluble antioxidants, such as ascorbyl palmitate, butylated hydroxyanisole (BHA), butylated hydroxytoluene (BHT), lecithin, propyl gallate, alpha-tocopherol and the like; and the metal chelating agents, such as citric acid, ethylenediamine tetraacetic acid (EDTA), sorbitol, tartaric acid, phosphoric acid and the like.

By a "therapeutically-effective amount" of a dopaminergic agent is meant a sufficient amount of the compound to treat dopamine-related disorders at a reasonable benefit/risk ratio applicable to any medical treatment. It will be understood, however, that the total daily usage of the compounds and compositions of the present invention will be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known in the medical arts.

The term "affective disorder" as used herein refers to disorders that are characterized by changes in mood as the primary clinical manifestation, for example, depression.

The term "anti psychotic agent" as used herein refers to drugs used extensively in the symptomatic management of all forms of schizophrenia, organic psychosis, the manic phase of manic depressive illness and other acute idiopathic illnesses and occasionally used in depression or in severe anxiety.

The term "attention deficit disorder" refers to a recently-classified pediatric neuropsychiatric disorder characterized by inattention, impulsivity, distractibility and sometimes hyperactivity, which replaces the less formal diagnoses of hyperactivity syndrome, hyperkinetic syndrome, minimal brain dysfunction and specific learning disability. The disorder is prevalent among pre-adolescent children and is reflected in poor school performance and social behavior and has been described in experimental reports of impaired perceptual, cognitive and motor function.

The term "cognitive impairment" refers to a deficiency in any of the aspects of the is cognitive (information processing) functions of perceiving, thinking and remembering.

The term "dopamine-related cardiovascular disorders" as used herein refers to conditions which can be reversed or improved by administration of dopamine or a dopaminergic agent, either alone or in combination therapy with other classes of cardiovascular agents. The usefulness of dopaminergic agents in cardiovascular diseases, for example in the treatment of shock and congestive heart failure, is based on the known, but incompletely understood, role of dopamine in the cardiovascular system, especially the effects of dopamine on the heart and the ability of dopamine to produce vasoconstriction while maintaining blood flow through renal and mesenteric beds. Also included are other related, potential uses for dopaminergic agents which include, for example, use in renal failure.

The term "dopamine-related neurological and psychological disorders" as used herein refers to behavioral disorders, such as psychoses and addictive behavior disorders; affective disorders, such as major depression; and movement disorders, such as Parkinson's Disease, Huntington's Disease and Gilles de la Tourette's syndrome; which have been linked, pharmacologically and/or clinically, to either insufficient or excessive functional dopaminergic activity In the CNS. Also included are miscellaneous indications for which dopaminergic agents have been found to be clinically useful. Examples of such indications include disorders characterized by vomiting, such as uremia, gastroenteritis, carcinomatosis, radiation sickness, and emesis caused by a variety of drugs; intractable hiccough and alcoholic hallucinosis.

"Normal dopamine levels" are those levels of dopamine that are found in the brains of control subjects and are usually measured as levels of the dopamine metabolites homovanillic acid (3-methoxy-4-hydroxphenylacetic acid) and 3,4-dihydroxyphenylacetic acid. Abnormal dopamine levels are those levels that are not within the range of dopamine levels found in the brains of control subjects.

The term "substance abuse" is used herein to mean periodic or regular self-administration of psychoactive substances in the absence of medical indications and despite the presence of persistent or recurrent social, occupational, psychological or physical problems that the person knows are caused by or may be exacerbated by continued use of the substance.

The total daily dose of the compounds of this invention administered to a host in single or in divided doses may be in amounts, for example, from 0.01 to 50 mg/kg body weight or more, usually from 0.1 to 30 mg/kg body weight Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in multiple doses or in a single dose.

The compounds of the present invention may be administered alone or in combination or in concurrent therapy with other agents which affect the dopaminergic system, for example, L-dopa, amantadine, apomorphine or bromocryptine; and with cholinergic agents, for example, benztropine, biperiden, ethopromazine, procyclidine, trihexylphenidyl, and the like. The compounds of the present invention may also be co-administered with agents, for example, enzyme inhibitors, which block their metabolic transformation outside the CNS.

This invention also provides pharmaceutical compositions in unit dosage forms, comprising a therapeutically-effective amount of a compound (or compounds) of this invention in combination with a conventional pharmaceutical carrier.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally-acceptable diluent or solvent, for example, as a solution in 1,3-butanediol. Among the acceptable vehicles and solvents that may be employed are water, Ringers solution, U.S.P. and isotonic sodium chloride solution. In addition, sterile, fixed oils are conventionally employed as a solvent or suspending medium. For this purpose, any bland fixed oil may be employed, including synthetic mono- or diglycerides. Also, fatty acids, such as oleic acid, are used in the preparation of injectables.

The injectable formulation may be sterilized, for example, by filtration through a bacteria-retaining filter, or by incorporating sterilizing agents in the form of sterile solid compositions which may be dissolved or dispersed in sterile water or other sterile injectable medium lust prior to use.

In order to prolong the effect of a drug, it is often desirable to slow the absorption of a drug from subcutaneous or intramuscular injection. The most common way to accomplish this is to inject a suspension of the drug in a crystalline or amorphous material which has poor water solubility The rate of absorption of the drug becomes dependent on the rate of dissolution of the drug which is, in turn, dependent on the physical state of the drug, for example, the crystal size of the drug and its crystalline form. Another approach to delaying absorption of a drug is to administer the drug as a solution or suspension in oil.

Injectable depot forms may also be made by forming microcapsule matrices of drugs and biodegradable polymers, such as with polylactidle-polyglycolide.

Depending on the ratio of drug to polymer and the composition of the polymer, the rate of drug release may be controlled by this method. Examples of other biodegradable polymers include poly-orthoesters and polyanhydrides. The depot injectables can also be made by entrapping the drug in liposomes or microemulsions which are compatible with body tissues.

Suppositories for rectal administration of the drug may be prepared by mixing the drug with a suitable non irritating excipient, such as cocoa butter and polyethylene glycol, both of which are solid at ordinary temperature, but liquid at the rectal temperature and will therefore melt in the rectum, releasing the drug.

Solid dosage forms for oral administration may include capsules, tablets, pills, powders, pills and granules. In such solid dosage forms the active compound may be admixed with at least one inert diluent, such as sucrose, lactose or starch., such dosage forms may also comprise, as is normal practice, additional substances other than inert diluents, e.g., tableting lubricants and other tableting aids, such as magnesium stearate and microcrystalline cellulose.

In the case of capsules, tablets and pills, the dosage forms may also comprise buffering agents. Tablets and pills may additionally be prepared with enteric coatings and other release-controlling coatings.

Solid compositions of a similar type may also be employed as fillers in soft and hard-filled gelatin capsules using such excipients as lactose or milk sugar, as well as high molecular weight polyethylene glycols and the like.

Liquid dosage forms for oral administration may include pharmaceutically acceptable emulsions, microemulsions, solutions, suspensions, syrups and elixirs containing inert diluents commonly used in the art, such as water, such compositions may also comprise adjuvants, such as welling agents: emulsifying and suspending agents; sweetening, flavoring and perfuming agents.

If desired, the compounds of the present invention can be incorporated into slow release or targeted-delivery systems, such as polymer matrices, liposomes and microspheres.

The active compounds may also be in micro-encapsulated form with one or more excipients as noted above. The solid dosage forms of tablets, dragees, capsules, pills, and granules may be prepared with coatings and shells, such as enteric coatings and other coatings well-known in the pharmaceutical formulating art. They may optionally contain opacifying agents, and may also be of a composition that they release the active ingredient(s) only, or preferably, in a certain part of the intestinal tract, optionally In a delayed manner. Examples of embedding compositions which can be used include polymeric substances and waxes.

Dosage forms for topical or transdermal administration of a compound of this invention further include ointments, pastes, creams, lotions, gels, powders, solutions, sprays, inhalants or transdermal patches. The active component is admixed under sterile conditions with a pharmaceutically-acceptable carrier and any needed preservatives or buffers, as required. Ophthalmic formulations, ear drops, eye ointments, powders and solutions are also contemplated as being within the scope of this invention. Administration sublingually, from one or more of the above dosage forms, is also contemplated as a suitable mode of administration of the compounds of the invention.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to the compounds of this invention, excipients, such as lactose, talc, silicic acid, aluminum hydroxide, calcium silicates and polyamide powder, or mixtures of these substances. Sprays may additionally contain customary propellants, such as chlorofluorohydrocarbons or environmentally- and pharmaceutically-acceptable substitutes.

Transdermal patches have the added advantage of providing controlled delivery of a compound to the body. Such dosage forms may be made by dissolving or dispersing the compound in the proper medium. Absorption enhancers may also be used to increase the flux of the compound across the skin. The rate may be controlled by either providing a rate-controlling membrane or by dispersing the compound in a polymer matrix or gel.

The invention claimed is:

1. A mono-ester or asymmetrically substituted di-ester pro-drug of a dopamine $D_1$ agonist selected from the following formulas:

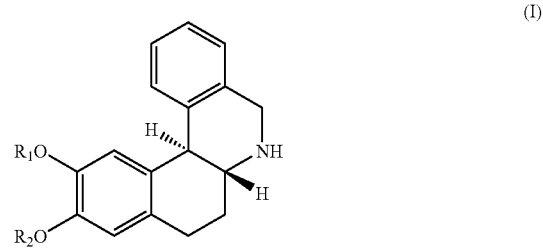

(I)

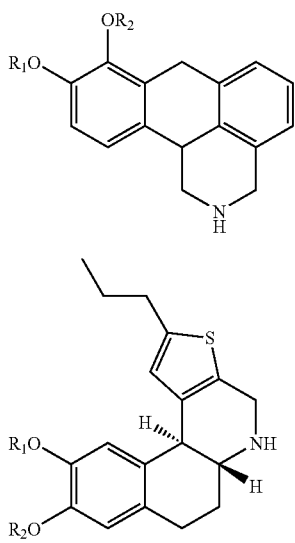

wherein one of $R_1$ and $R_2$ is hydrogen or acetyl and the other one is selected from the group consisting of $(C_3-C2)$alkanoyl; halo-$(C_3-C_{20})$alkanoyl; $(C_3-C_{20})$alkenoyl; $(C_4-C7)$cycloalkanoyl; $(C_3-C6)$-cycloalkyl $(C_2-C_{16})$alkanoyl; aroyl which is unsubstituted or substituted by 1 to 3 substituents selected from the group consisting of halogen, cyano, trifluoromethanesulphonyloxy, $(C_1-C_3)$alkyl, and $(C_1-C_3)$alkoxy, which latter may in turn be substituted by 1 to 3 halogen atoms; aryl$(C_2-C_{16})$alkanoyl which is unsubstituted or substituted in the aryl moiety by 1 to 3 substituents selected from the group consisting of halogen, $(C_1-C_3)$alkyl, and $(C_1-C_3)$alkoxy, which latter may in turn be substituted by 1 to 3 halogen atoms; and hetero-arylalkanoyl having one to three heteroatoms selected from oxygen, sulfur, and nitrogen in the heteroaryl moiety and 2 to 10 carbon atoms in the ailcanoyl moiety and which is unsubstituted or substituted in the heteroaryl moiety by 1 to 3 substituents selected from the group consisting of halogen, cyano, trifluoromethanesulphonyloxy, $(C_1-C_3)$alkyl, and $(C_1-C_3)$alkoxy, which latter may in turn be substituted by 1 to 3 halogen atoms, and the physiologically acceptable salts thereof;

providing that in Formula I, when one of $R_1$ and $R_2$ is hydrogen, the other one of $R_1$ and $R_2$ is not pivaloyl or benzoyl.

2. A compound of Formula I, wherein $R_1$ is acetyl and $R_2$ is pivaloyl.

3. A compound of Formula I, wherein $R_2$ is acetyl and $R_1$ is pivaloyl.

4. A compound of Formula II, wherein $R_1$ is hydrogen or acetyl and $R_2$ is pivaloyl.

5. A compound of Formula II, wherein $R_2$ is hydrogen or acetyl and $R_1$ is pivaloyl.

6. A compound of Formula III, wherein $R_1$ is hydrogen or acetyl and $R_2$ is pivaloyl.

7. A compound of Formula III, wherein $R_2$ is hydrogen or acetyl and $R_1$ is pivaloyl.

8. A pharmaceutical composition for selectively binding and activating dopaminergic $D_1$ receptors, said pharmaceutical composition comprising a pharmaceutically-acceptable carrier and a compound according to claim 1 in an amount sufficient to activate dopamine $D_1$ receptors.

9. A pharmaceutical composition for treating Parkinson's disease, characterized by abnormal dopaminergic activity and responsive to activation of dopamine $D_1$ receptors, said pharmaceutical composition comprising a pharmaceutically-acceptable carrier and an amount of a compound of claim 1 sufficient to activate dopamine $D_1$ receptors.

10. A method for treating Parkinson's disease, characterized by abnormal dopaminergic activity and responsive to activation of dopamine $D_1$ receptors, said method comprising the step of administering to a patient in need of such treatment a therapeutically effective amount of a compound according to claim 1.

* * * * *